United States Patent [19]

Huwiler et al.

[11] Patent Number: 4,503,234
[45] Date of Patent: Mar. 5, 1985

[54] PRODUCTION OF 2-(2-AMINOTHIAZOLE-4-YL)-2-(SYN)-METHOXYIMINO ACETIC ESTERS

[75] Inventors: Alfred Huwiler; Leander Tenud, both of Visp, Switzerland

[73] Assignee: Lonza Ltd., Gampel, Switzerland

[21] Appl. No.: 286,636

[22] Filed: Jul. 24, 1981

[30] Foreign Application Priority Data

Jul. 24, 1980 [CH] Switzerland ............... 5658/80

[51] Int. Cl.³ ........................................... C07D 277/40
[52] U.S. Cl. .................................................. 548/194
[58] Field of Search ........................................ 548/194

[56] References Cited

U.S. PATENT DOCUMENTS

| | | | |
|---|---|---|---|
| 3,971,778 | 7/1976 | Cook et al. | 260/243 |
| 4,097,595 | 6/1978 | Heymes | 424/246 |
| 4,098,888 | 7/1978 | Ochiai et al. | 424/246 |
| 4,203,899 | 5/1980 | Ochiai et al. | 548/194 |
| 4,205,180 | 5/1980 | Ochiai et al. | 560/168 |
| 4,278,671 | 7/1981 | Ochiai et al. | 424/246 |
| 4,304,770 | 12/1981 | Takaya et al. | 424/246 |

FOREIGN PATENT DOCUMENTS

| | | |
|---|---|---|
| 2805655 | 8/1978 | Fed. Rep. of Germany . |
| 42885 | 4/1976 | Japan . |
| 1389195 | 4/1975 | United Kingdom . |
| 1389194 | 4/1975 | United Kingdom . |
| 1399088 | 5/1975 | United Kingdom . |
| 1399086 | 6/1975 | United Kingdom . |

OTHER PUBLICATIONS

Wise, Richard et al., "Preliminary Report on the In Vitro Study of HR 756", 24 pages.
Van Landuyt, et al., Abstract, p. 79.
Van Landuyt, H. W., et al., "In Vitro Activity of Cefatoxime etc.", 15 pages.
Heymes, R., et al., "Considerable Magnification of the Antibacterial Activity of Cephalosporin Derivatives etc.", 10 pages.
Elks, J., (Ed.), "Recent Advances in the Chemistry of β-Lactam Antibiotics", Glaxo Research Ltd., Publ. No. 28, (1977), Chapter 15, pp. 145 to 152.
Zinacef 250, -750, -1500, (Hoechst AG and Glaxo GmbH), 106, 12/15/77, 4 pages.
"Unlisted Drugs", vol. 27, No. 12, (Dec. 1975), p. 191.
Fu, Kwung P., et al., "Beta-Lactamase of HR 756, a Novel Cephalosporin Compared to that of Cefuroxime and Cefoxitin", Antimicr. Agents and Chemo., vol. 14, (Sep. 1978), pp. 322 to 326.
Bucourt, Robert, et al., "Proprietes Antibiotique Inattendues Dans le Domaine des Cephalosphorines", C. R. Acad. Se. Paris, vol. 284, (May 9, 1977), pp. 1847 to 1849.
Drasar, R. A., et al., "Activity of HR 756 Against Haemophilus Influenza, Bacteroides fragilis and Gram-Negative Rods", J. Of. Antimicro. Chemo., vol. 4, 1978, pp. 445 to 450.
Chabbert, Yves A., et al., "HR 756, The Syn Isomer of a New Methoxyimino Cephalosporin with Unusual Antibacterial Activity", Antimicrobial Agents and Chemotherapy, (Nov. 1978), pp. 749 to 754.
Hamilton-Miller, J. M. T., et al., "Cefotamine (HR 756) a new Cephalosporin with Exceptional Broad-Spectrum Activity In Vitro", J. Antimicro. Chemoth., vol. 4, (1978), pp. 437 to 444.
Vanhoof, R., et al., "In-Vitro Activity of New Cephalosporin (HR 756) and Cefazolin", The Lancet, (Jul. 22, 1978), pp. 209 and 210.
Stratford, Bryan C., "In-Vitro Activity of New Cephalosphorin (HR 756), and Cefazolin", The Lancet, (Sep. 1978), pp. 528 and 529.
Courtieu, A. L., et al., "Laboratory Evaluation of HR 756-A New Semi-Synthetic Cephalosporin, (six pages), Sep. 28, 1978, presented at 1st Int. Congress of the Mediterranean Society of Chemotherapy, Madrid, Spain.

*Primary Examiner*—Robert Gerstl
*Attorney, Agent, or Firm*—Fisher, Christen & Sabol

[57] ABSTRACT

Process for the production of 2-(2-aminothiazole-4-yl)-2-(syn)-methoxyimino acetic ester. First 4-chloroacetoacetic ester is oximized and then the resultant chlorohydroxyimino ester, in solution form, reacted with thiourea to produce 2-(2-aminothiazole-4-yl)-2-(syn)-hydroxyimino acetic ester. The latter is methylated with dimethyl sulfate using phase transfer catalysis.

5 Claims, No Drawings

PRODUCTION OF 2-(2-AMINOTHIAZOLE-4-YL)-2-(SYN)-METHOXYIMINO ACETIC ESTERS

BACKGROUND OF THIS INVENTION

1. Field of This Invention

This invention is related to the production of 2-(2-aminothiazole-4-yl)-2-(syn)-methoxyimino acetic ester which, together with its derivatives, forms side chains of semisynthetic cephalosporins of the third generation. As such, these substances are of increasing importance.

2. Prior Art

In the case of the previously known production processes, one can differentiate between three synthesis ways. German patent document (open to public inspection) Nos. 28 12 625 and 28 31 332 or the French patent application Nos. 2,390,442 and 2,384,781, teach the following synthesis route: The acetoacetic ester is oximized, halogenated and reacted with thiourea into hydroxyiminothiazole acetic ester. The latter is then converted with diazomethane or dimethyl sulfate (without the use of the phase transfer catalysis of the process of this invention) into methoxyiminothiazolyl acetic ester.

German OS Nos. 27 15 385 and 28 05 655 disclose the following procedure: The oxyiminoacetoacetic ester is methylated, halogenated and then reacted with thiourea.

In the third synthesis method, the oxyiminoacetoacetic ester is first halogenated, then methylated and subsequently reacted with thiourea into methoxyiminothiazolyl acetic ester. This method of operation is taught by German OS No. 28 06 226 and the French patent application Nos. 2,381,053 and 2,384,779.

In the case of all of such synthesis methods, a mixture of syn- and anti-products is obtained:

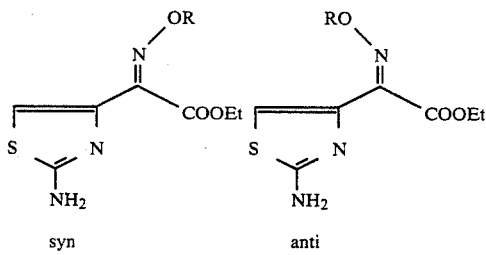

syn anti

For use in connection with semisynthetic cephalosporins, i.e., for reaction with 7-aminocephalosporanic acid, however only the syn-isomeric is desired.

BROAD DESCRIPTION OF THIS INVENTION

An object of this invention is to provide a process which avoids the above-stated disadvantage of the prior art methods. Other objects and advantages of this invention are set out herein or are obvious herefrom to one ordinarily skilled in the art.

The objects and advantages of this invention are achieved by the method of this invention.

This invention involves a process for the production of 2-(2-aminothiazole-4-yl)-2-(syn)-methoxyimino acetic esters. The process includes oximizing 4-chloroacetoacetic ester. The resultant chlorohydroxyimino ester, in solution form, is directly reacted with thiourea to produce 2-(2-aminothiazole-4-yl)-2-(syn)-hydroxyimino acetic ester. The latter is methylated with dimethyl sulfate using phase transfer catalysis.

Preferably the oximation of the 4-chloroacetoacetic ester is conducted using an alkali nitrite in glacial acetic acid at a starting temperature of 0° C. Preferably the solution obtained from the oximation, which has a temperature of below 0° C., is introduced directly into an aqueous thiourea solution in such a manner that the reaction temperature does not rise above +40° C. Also, preferably the 2-(2-aminothiazole-4-yl)-2-(syn)-hydroxyimino acetic ester is reacted by means of phase transfer catalysis with dimethyl sulfate at a temperature between 0° C. and +5° C. Preferably the 2-(2-aminothiazole-4-yl)-2-(syn)-hydroxyimino acetic ester is suspended together with tetrabutyl ammonium hydrogen sulfate in acetone and, after mixing this suspension with concentrated alkali it is methylated in acetone by adding dimethyl sulfate.

As compared to the known processes, the process according to this invention has the following advantages:

1. The invention process produces only the desired syn-product in isomerically pure form.
2. The hydroxyiminothiazolyl acetic ester can be produced in one step without isolation of the intermediate product.
3. The methylation of the hydroxyiminothiazolyl acetic ester is accomplished by means of phase transfer catalysis. As a result of that, the yield in this step may be increased from 40 to 50 percent to 80 percent.

DETAILED DESCRIPTION OF THIS INVENTION

As used herein, all parts, percentages, ratios and proportions are on a weight basis unless otherwise stated herein or otherwise obvious herefrom to one ordinarily skilled in the art.

The process of this invention has the following reaction sequence.

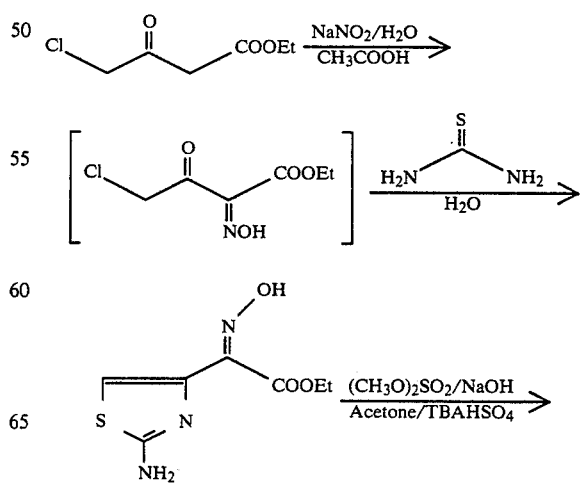

-continued

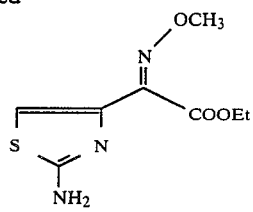

(TBAHSO₄ is tetrabutyl ammonium hydrogen sulfate.)

The process of this invention is carried out preferably in such a way that, in a first phase, 4-chloroacetoacetic ester together with glacial acetic acid is cooled to 0° C. and is oximated with an alkali nitrite, preferably with sodium nitrite. Other useful alkali nitrites include potassium nitrite and lithium nitrite. The oximation must be accomplished under cooling so that the temperature in the reaction medium, after the addition of nitrite is completed, is about −15° C. At this temperature, the 4-chloro-2-hydroxyiminoacetoacetic ester formed is then reacted (without isolating it) with thiourea directly into the 2-(2-aminothiazole-4-yl)-2-(syn)-hydroxyimino acetic ester. The thiourea is preferably dissolved in water. Effectively, the addition of the 4-chloro-2-hydroxyiminoacetoacetic ester to the thiourea solution is carried out in such a way that the reaction temperature does not rise above +40° C.

In a second phase the 2-(2-aminothiazole-4-yl)-2-(syn)-hydroxyimino acetic ester is suspended effectively together with a phase transfer catalyst in an organic solvent, is mixed with caustic soda solution and is methylated with dimethyl sulfate to give 2-(2-aminothiazole-4-yl)-2-(syn)-methoxyimino acetic ester. The preferred reaction temperature in this second phase is around 0° C. Quaternary ammonium salts or phosphonium salts, preferably however, tetrabutyl ammonium hydrogen sulfate, can be used as the phase transfer catalyst. Examples of such phase transfer catalysts are cetylpyridinium chloride, cetyldimethylbenzylammonium chloride, p-tertiaryoctyl-phenoxy-ethoxyethyldimethylbenzylammonium chloride, alkyl ($C_1$ to $C_6$) quaternary ammonium sulfates and halides, and tetrahydroxymethylphosphonium chloride.

As organic solvents, besides, the preferred acetone, aprotic solvents miscible with water and organic solvents not miscible with water can be used. The dipolar aprotic solvent usually will have a dielectric constant which lies between 20 and 50. Examples of useful aprotic solvents are dimethyl sulfoxide, dimethyl formamide, acetone, diethyl sulfoxide, dimethylacetamide, acetonitrile, benzonitrile, formamide, methyl propionamide, sulfolane, N-methyl formamide, dimethyl sulfone, tetramethylsulfone, tetrahydrofuran, 1,2-dimethoxyethane and mixtures of these solvents. Examples of useful organic solvents are diisobutyl ketone, n-hexyl alcohol, n-octyl alcohol, benzene, cyclohexane, isopropylbenzene and monochlorobenzene.

By way of summary, this invention involves a process for the production of 2-(2-aminothiazole-4-yl)-2-(syn)-methoxyimino acetic ester. 4-chloroacetoacetic ester is oximized in a first step with sodium nitrite and the intermediate product, a chlorohydroxyimino ester, without isolating it, is reacted directly with thiourea into 2-(2-aminothiazole-4-yl)-2-(syn)-hydroxyimino acetic ester. This ester is then converted in a second step with dimethyl sulfate and with the aid of a phase transfer catalyst into the desired end product.

EXAMPLE

Phase I

Production of 2-(2-aminothiazole-4-yl)-2-(syn)-hydroxyimino acetic ester:

174.0 g (1.0 mole) of 4-chloroacetoacetic ester and 176.0 g of glacial acetic acid were placed in a 500 ml sulfurizing flask. The mixture was cooled to 0° C. During a 45 minute period, a solution of 72.8 g of 99% sodium nitrite (1.05 mole) in 102.0 g of water was added drop by drop to this solution while cooling in such a way that the inside temperature dropped slowly and, after the dosing in was completed, reached −15° C. The dark red solution of 4-chloro-2-hydroxyiminoacetoacetic ester thus obtained was then stirred additionally for 2 hours at this temperature. During this time, a solution of 76.1 g (1.0 mole) of thiourea in 610.0 g of water was prepared in a 1500 ml flask and was heated to between 30° to 35° C. Then the solution of 4-chloro-2-hydroxyiminoacetoacetic ester, still having a temperature of −15° C., was introduced by means of a dosing pump into the aqueous thiourea solution over a 45 minute period in such a way that the reaction temperature slowly climbed to +40° C., but never exceeded this temperature. After the dosing in was completed, the mixture was still stirred for 4 hours. During this time the 2-(2-aminothiazole-4-yl)-2-(syn)-hydroxyimino acetic ester slowly deposited. The ester was subsequently filtered off, was washed with 1 liter of water and was dried overnight under vacuum (approx. 14 mbar) in a drying cabinet at 50° C.

Thus, 144.2 g of yellowish crystals of the 2-(2-aminothiazole-4-yl)-2-(syn)-hydroxyimino acetic ester with a melting point of 185° to 186° C. were obtained. The yield amounted to 67 percent, related to 4-chloroacetoacetic ester. The product has a syn-configuration [NMR(DMSO-$d_6$, 60 MHz): 11.7 ppm (N-OH); 6.9 ppm (proton of the thiazole ring)].

Phase II 10.7 g (48 mmole) of 2-(2-aminothiazole-4-yl)-2-(syn)-hydroxyimino acetic ester and 1.7 g (5 mmole) of tetrabutyl ammonium hydrogen sulfate were placed in 56.0 g of acetone in a 250 ml 3-necked flask. The mixture was cooled to 0° C.

Within a few minutes, 5.0 g of 50 percent caustic soda solution was added to this suspension and the mixture thus obtained was stirred at 5° C. for 30 minutes. Then, a solution of 7.6 g (60 mmole) of dimethyl sulfate in acetone was added drop by drop. The reaction mixture was stirred during an additional 3 hours at °C. and filtered free of undissolved matter. By evaporating the filtrate in a vacuum of about 14 mbar at about 30° C., a residue was obtained. The residue was suspended in 150 g of water, was drained off and was dried overnight in a drying cabinet under a vacuum of 14 mbar at 50° C.

In this manner, 8.9 g of brownish crystals of 2-(2-aminothiazole-4-yl)-2-(syn)-methoxyimino acetic ester having a melting point of 155° to 157° C. was obtained. This corresponds to a yield of 80 percent, related to the 2-(2-aminothiazole-4-yl)-(syn)-hydroxyimino acetic ester. The product had a syn-configuration [NMR(DMSO-$d_6$, 60 MHz): 6.95 ppm (proton of the thiazole ring); 3.9 ppm (N-OCH₃)]. After crystallization from methanol-water the melting point was 160°–161° C.

What is claimed is:

1. Process for the production of 2-(2-aminothiazole-4-yl)-2-(syn)-methoxyimino acetic ester consisting essentially of (a) oximizing 4-chloroacetoacetic ester, 4-chloro-2-hydroxyiminoacetoacetic ester resulting, (b) reacting the resultant 4-chloro-2-hydroxyiminoacetoacetic ester, without isolation, directly with thiourea in the presence of water at a temperature which does not exceed +40° C., 2-(2-aminothiazole-4-yl)-2-(syn)-hydroxyimino acetic ester, resulting at a temperature which does not exceed +40° C., and methylating the 2-(2-aminothiazole-4-yl)-2-(syn)-hydroxyimino acetic ester with dimethyl sulfate using a phase transfer catalyst in the presence of an aprotic organic solvent and an alkali lye at a temperature between 0° C. and +5° C.

2. Process as claimed in claim 1 wherein the solution obtained from the oximation, which has a temperature of below 0° C., is introduced directly into an aqueous thiourea solution in such a way that the reaction temperature does not rise above +40° C.

3. Process as claimed in claim 1 wherein the 2-(2-aminothiazole-4-yl)-2-(syn)-hydroxyimino acetic ester is suspended together with tetrabutylammoniumhydrogen sulfate in acetone, and after mixing this suspension with alkali lye, it is methylated in acetone by adding dimethyl sulfate.

4. Process as claimed in claim 1 wherein the phase transfer solvent is an alkyl quaternary ammonium sulfate, the alkyl having 1 to 6 carbon atoms, or an alkyl quaternary ammonium halide, the alkyl having 1 to 6 carbon atoms.

5. Process as claimed in claim 1 wherein the aprotic organic solvent is a dipolar aprotic organic solvent having a dielectric constant between 20 and 50.

* * * * *